United States Patent [19]
Liotta et al.

[11] Patent Number: 4,801,728
[45] Date of Patent: Jan. 31, 1989

[54] OMEGA-PHASE CATALYZED CHEMICAL REACTIONS

[75] Inventors: Charles L. Liotta; Edward M. Burgess, both of Marietta, Ga.

[73] Assignee: M&T Chemicals Inc., Woodbridge, N.J.

[21] Appl. No.: 878,166

[22] Filed: Jun. 25, 1986

Related U.S. Application Data

[63] Continuation-in-part of Ser. No. 740,652, Jun. 3, 1985, abandoned.

[51] Int. Cl.$^4$ .................. C07C 120/04; C07C 121/75
[52] U.S. Cl. ..................................... 558/348; 560/104; 558/332; 558/343; 558/349
[58] Field of Search ............... 558/332, 343, 348, 349; 560/104

[56] References Cited

U.S. PATENT DOCUMENTS 2,553,404  5/1951  Dixon .................................. 558/348
2,915,548  12/1959  Andres ................................ 558/348

FOREIGN PATENT DOCUMENTS 15427  9/1980  European Pat. Off. .
78709  5/1983  European Pat. Off. .
97357  1/1984  European Pat. Off. .
60-90052  7/1981  Japan .

Primary Examiner—Paul J. Killos
Attorney, Agent, or Firm—S. A. Marcus; W. Katz

[57] ABSTRACT

The present invention relates to reaction mixtures and processes which employ an ω-phase catalyst for carrying out displacement reactions at a substantially enhanced rate.

6 Claims, 1 Drawing Sheet

FORMATION OF REACTION MIXTURE

– 4,801,728 –

OMEGA-PHASE CATALYZED CHEMICAL REACTIONS

REFERENCE TO COPENDING APPLICATION

This application is a continuation-in-part of copending application Ser. No. 740,652 filed June 3, 1985, now abandoned.

BACKGROUND OF THE INVENTION

1. Field of the Invention

The present invention relates to reaction mixtures and processes which employ an $\omega$-phase catalyst for carrying out displacement reactions at a substantially enhanced rate.

2. Description of the Prior Art

The use of phase transfer catalysts to bring together two mutually insoluble reagents in sufficient concentration to attain conveniently rapid reaction rates has been described in the literature. C. Starks and C. Liotta, *Phase Transfer Catalysis* (1978); W. Weber and G. Gokel, *Phase Transfer Catalysts in Organic Synthesis* (1980); E. Dehmlow and S. Dehmlow, *Phase Transfer Catalysis* (1983); and H. A. Zahalka and Y. Sasson, J. Chem. Soc. Commun. (1984), p. 1652.

Generally a phase transfer catalyst functions as a vehicle for transferring the anion of a metal salt from the aqueous or solid phase into the organic phase wherein reaction can occur with an organic reactant dissolved therein. Accordingly, it has been assumed that the rate of reaction is proportional to the concentration of catalyst in the organic phase. In this medium, it is known that water influences the course of the reaction; often its role is found to be disadvantageous. Even in those instances where water may be considered helpful, its role is not well understood or defined.

Accordingly, it is an object of this invention to provide reaction mixtures, and processes using such mixtures, for carrying out phase transfer catalyzed chemical reactions at a substantially enhanced rate.

Another object of the invention is to provide such reaction mixtures in which an $\omega$-phase catalyst enables displacement and addition reactions to proceed at a substantially enhanced rate.

A further object herein is to provide a process in which the reaction product can be easily recovered.

A feature of the present invention is the formation of an $\omega$-phase catalyst in undiluted form by retention of substantially all of a phase transfer catalyst material present in the system in a polar liquid which itself is adsorbed on an inorganic salt.

These and other objects and features of the invention will be made apparent from the following more particular description of the invention.

SUMMARY OF THE INVENTION

This invention is based upon the discovery that displacement reactions which are catalyzed by phase transfer catalysts in conventional liquid-liquid or liquid-solid phase systems can be carried out more advantageously by forming an undiluted $\omega$-phase catalyst which enables such reactions to occur at a maximum rate.

The $\omega$-phase catalyst of the invention is formed by retention of a conventional phase transfer type catalyst material in a polar liquid which, in turn, is adsorbed on an inorganic salt. The quantity of the polar liquid is predetermined so that substantially all of the catalyst material is present in the form of undiluted $\omega$-phase catalyst. The thus-formed $\omega$-catalyst is attracted to the cation of the salt thereby enabling its anion to become available for reaction with an organic reactant. The organic reactant is present in an organic solvent in the mixture. Reaction then occurs at the interface between said solvent and the polar liquid.

The water-catalyst system activates the anionic portion of the metal salt by complexing with the cationic portion of the metal salt. The composite water-catalyst-activated salt system located on the surface of the solid salt is the $\omega$-phase.

The reaction proceeds at a maximum rate because the quantity of polar liquid present is sufficient to extract substantially all of the phase transfer material from the organic phase to form the $\omega$-catalyst without diluting it. In the preferred embodiment of the invention, the polar liquid is water present in a quantity of about 1-2 ml per 0.01 mole of phase transfer type catalyst material, e.g. 5 eq. $H_2O$ per eq. crown ether catalyst. The typical chemical reactions herein are displacement reactions, such as the formation of nitriles from alkyl or aralkyl halides.

DETAILED DESCRIPTION OF THE INVENTION

Figure 1:
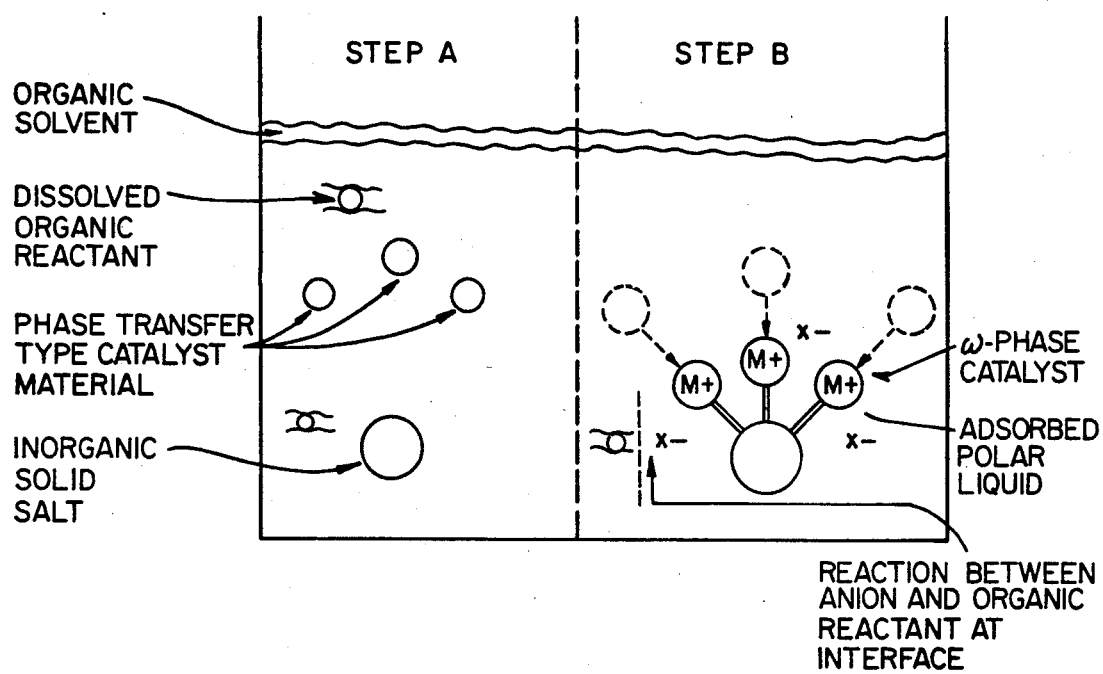
FIG. 1 is a schematic representation of the formation of the $\omega$-phase catalyst system of the present invention.

Referring now to the drawings, there is shown in FIG. 1 a schematic representation of the formation of the $\omega$-phase catalyst system in the reaction mixture of the present invention. In step A an inorganic solid salt is suspended in an organic solvent. For a displacement reaction, for example, the salt is a metal cyanide or halide, for example, sodium or potassium cyanide, lithium, calcium and magnesium salts also may be used. The salt is capable of dissociating into a cation and a cyanide anion reactant. The organic reactant shown in step A is a reactive alkyl or aralkyl halide, such as 1-bromohexane, benzene chloride or benzyl bromide, which is dissolved in a non-polar solvent, suitably an organic solvent such as benzene, toluene, methylene dichloride, tetrahydrofuran, diemethylformamide and the like.

The phase transfer catalyst material then is dissolved in the organic solvent. Suitable catalysts include macrocyclic ethers, such as crown ethers; quaternary ammonium and phosphonium salts; macrobicyclic ethers, linear polyethers, such as dialkylpolyethylene oxides; cryptates, and the like. The catalyst is present in a suitable amount in the mixture for catalytic action.

In step B, as shown, a polar liquid, for example, water, is added in a predetermined quantity to the reaction mixture and is adsorbed on the inorganic solid forming an $\omega$-phase thereon. The amount of water added is suitable to extract substantially all of the phase transfer type catalyst material from the organic solvent and to retain in undiluted form. As shown in the graph in FIG. 2, this predetermined amount of water provides an enhanced rate of reaction.

The combination of the phase transfer catalyst material retained in water adsorbed on the solid salt is referred to herein as the "ω-phase catalyst". Unlike conventional phase transfer catalysts, which transfer anions into the organic phase for reaction, in ω-phase catalysis for reaction with the organic reactant such reaction takes place within the ω-phase catalyst. It is apparent that there is no anion transfer into an organic phase in the catalysis of this invention.

The reaction between the available anion reactant and the organic reactant occurs rapidly at elevated temperatures to give a quantitative yield of the desired product. The product remains dissolved in the organic solvent free of catalyst. The resultant reaction mixture then is filtered and the product is recovered from the filtrate by fractional distillation. As a feature of this invention, the product recovery step does not require separation of catalyst from the product; instead the ω-phase catalyst remains with the solid.

Figure 2:
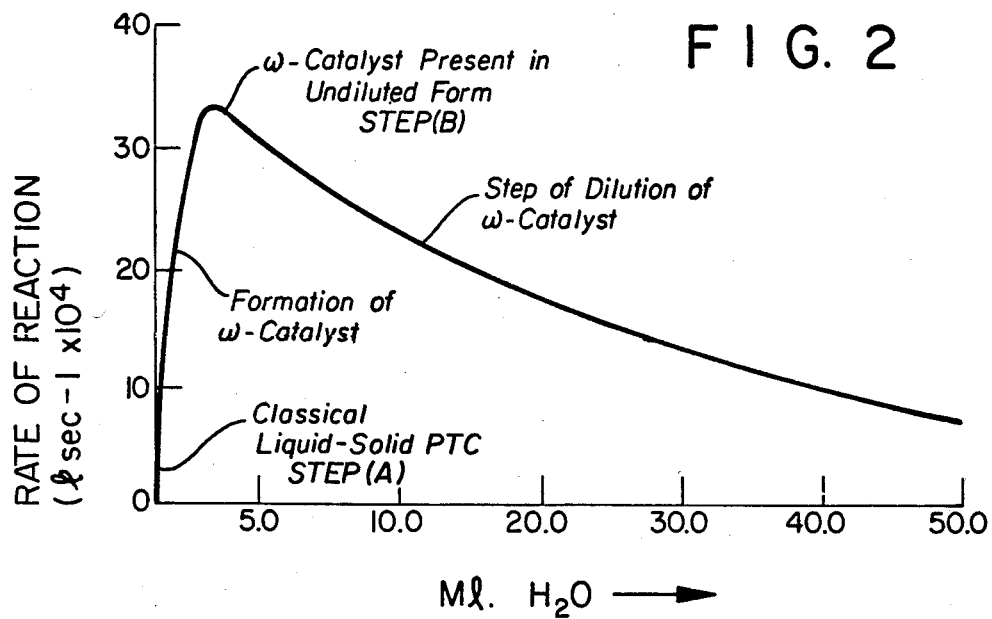
FIG. 2 is a graph of rate of reaction (k $sec^{-1}$) vs. quantity of water (ml.) present in the reaction mixture for the 18-crown-6 ether catalyzed reaction of benzyl chloride and potassium cyanide in toluene solvent.

Referring now to FIG. 2, there is shown a graph of the rate of reaction vs. the quantity of water added to the reaction mixture. Without added water, a classical liquid-solid phase transfer catalysis reaction situation (A) is present in which the rate of reaction is very low. As water is added to the reaction mixture in step (B), the phase transfer catalyst material is extracted from the organic phase to form an ω-phase catalyst on the adsorbed water. The quantity of water added is sufficient to extract substantially all of the catalyst material from the organic phase into the ω-phase as an ω-phase catalyst without diluting it. The thus-formed ω-phase catalyst now is present in undiluted form in the reaction mixture. At this point in the addition of water, the rate of reaction is at a maximum; thereafter additional water merely serves to dilute the ω-phase catalyst and the rate declines appreciably.

The preferred quantity of added water to achieve a maximum rate of reaction usually is about 1 ml. water per 0.01 mole of catalyst material present; e.g. 5 eq. $H_2O$ per eq. of crown.

The invention will be illustrated with references to the following examples.

EXAMPLE 1

Reaction of Benzyl Chloride with KCN Catalyzed with Tetra-n-Butyl Ammonium Chloride Dry KCN (10.0 g, 0.15 mole), KCl (11.2 g, 0.15 mole), and tetra-n-butyl ammonium chloride (1.45 g, 0.0052 mole) were placed into a flask and sealed. A nitrogen inlet tube was attached to the flask (to prevent absorption of water) and a thermometer was inserted. Then water (1.0 ml) and toluene (40.0 ml) were added and the flask was immersed into a water bath maintained at a temperature of 85±0.05° C. Stirring was commenced and after ½ hour, a solution of benzyl chloride (6.0 ml, 0.052 mole) and anisole (2.0 ml, 0.018 mole) as a standard were added. At various intervals, an aliquot (0.05 mol.) was removed and analyzed by glc. The column was a fused silica capillary column (DB-1) with a film thickness of 0.25 um., column dimensions of 30 m.×0.252 mm. The column temperature was 100° C., injection port 250° C., and detector port 250° C. The retention time of the compounds of interest was: anisole 3.41 min., benzyl chloride 4.83 min., benzyl cyanide 7.37 min.

The glc data showed that the reaction was complete within a half-hour. The yield of the benzyl cyanide product was essentially quantitative and free of catalyst; the product was recovered by fractional distillation from the solvent.

EXAMPLE 2

Example 1 was repeated using KOH/KI solids in place of KOH/KBr solids with similar results.

EXAMPLE 3

The reaction described in Example 1 was repeated using 18-crown-6 ether as the catalyst in place of tetra-n-butylammonium chloride to provide a similar yield of product.

EXAMPLE 4

The reaction described in Example 1 was repeated with varying amounts of added water. The concentration of the tetra-n-butylammonium chloride was determined in the following manner:

A 3-neck, round-bottom flask is equipment with a mechanical stirrer, a nitrogen inlet tube and a rubber septum. The flask was charged with dry benzene (50.0 ml.) and tetra-n-butylammonium chloride (1.45 g., 5.2 moles). After each change in condition (addition of salt or water) the solution was allowed to equilibrate for ½ hour at room temperature and at a stirring rate of 1500 rpm. The salts used are KCl (11.2 g., 0.15 mole) and KCN (10.0 g., 0.15 mole). The analysis is performed by a 60 mhz. nmr. to determine ratio of benzene to quaternary salt in the organic phase.

Table I below contains data on the distribution of the quaternary ammonium salt between the organic phase and the ω-phase in the presence of varying quantities of water.

TABLE I

| $H_2O$ (ml.) | % quat. in organic phase |
|---|---|
| 0 | 100.0 |
| 0 | 94.6 |
| 0.2 | 89.9 |
| 0.4 | 19.0 |
| 1.0 | 1 |
| 5.0 | 0 |

*no salt present

The data shows that after the addition of less than 1.0 ml. of water, essentially all of the quaternary salt has disappeared from the organic phase as is in the ω-phase.

The catalytic effect of these systems in the reaction of cyanide ion with benzyl chloride is shown in Table II below.

TABLE II

| $H_2O$ (ml) | $K \times 10^4$ |
|---|---|
| 0.0 | 0.001 |
| 0.1 | 0.093 |
| 0.4 | 0.682 |
| 0.5 | 0.973 |
| 0.8 | 1.36 |
| 1.0 | 14.2 |
| 2.5 | 28.7 |
| 5.0 | 27.8 |
| 10.0 | 22.2 |
| 20.0 | 24.2 |
| 30.0 | 17.8 |
| 40.0 | 14.6 |
| 50.0 | 5.3 |

The rate constant k was determined as described below by plotting ln ($PhCH_2Cl_t/PhCH_2Cl_{t-o}$) vs time. All of the rate constants are first order with respect to benzyl chloride except at water amounts below 1.0 ml.

What is claimed is:

1. A reaction mixture for carrying out catalyzed displacement chemical reactions between an organic reactant and an inorganic anion at rapid rates comprising:
   (a) a solid inorganic salt-selected from an alkali or alkaline earth metal halide, nitrile, hydroxide or acetate which is capable of dissociating into a cation and an anion reactant,
   (b) a polar liquid which is selected from water, ethylene glycol, glyceryl and dimethylformamide present in a pre-determined quantity which is adsorbed on said solid,
   (c) a w-phase catalyst which comprises a phase transfer type catalyst material selected from a macrocyclic or macrobicyclic ether, a linear polyether or a quaternary salt which is retained in said adsorbed polar liquid and attracted to said cation thereby enabling said anion to be available for reaction, the quantity of said polar liquid being predetermined so that substantially all of said catalyst material is present in the form of undiluted w-catalyst,
   (d) a non-polar organic solvent which forms an interface with said polar liquid, and
   (e) an organic reactant selected from a reactive alkyl-aryl or aralkyl halide dissolved in said solvent, whereby chemical action can occur between said anion and said organic reactant at an enhanced rate with a given amount of catalyst material.

2. A reaction mixture according to claim 1 in which the predetermined quantity of said polar liquid is 5 eq. $H_2O$ per eq. of phase transfer catalyst.

3. A reaction mixture according to claim 1 in which the predetermined quantity of said polar liquid is about 1-2 ml of water per 0.01 mole of said phase transfer catalyst.

4. A reaction mixture according to claim 1 in which said organic solvent is benzene or toluene.

5. A process of carrying out $\omega$-phase catalyzed reactions at maximum rate and high yield which comprises providing the reaction mixture of claim 1, heating said mixture at a selected temperature for a given period of time, filtering the resultant mixture and separating the product directly from the catalyst-free solvent.

6. A process according to claim 5 in which said reaction is a displacement reaction, the polar liquid is water, the solid reactant is an inorganic salt, the catalyst material is a crown ether or a quaternary salt and the organic reactant is an organic halide.

* * * * *